United States Patent [19]

Price et al.

[11] 4,239,769
[45] Dec. 16, 1980

[54] PHARMACOLOGICALLY ACTIVE COMPOUNDS

[75] Inventors: Barry J. Price, Hertford; John W. Clitherow, Sawbridgeworth; Michael D. Dowle, Ware; Roger Hayes, Digswell; John Bradshaw, Ware, all of England

[73] Assignee: Allen & Hanburys Limited, London, England

[21] Appl. No.: 903,116

[22] Filed: May 5, 1978

[30] Foreign Application Priority Data

May 17, 1977 [GB] United Kingdom ............... 20659/77

[51] Int. Cl.³ ................ A61K 31/38; C07D 333/20; C07D 333/24; C07D 409/06
[52] U.S. Cl. ........................ 424/274; 260/326.35; 260/326.5 SM; 260/326.82; 260/326.84; 424/275; 542/416; 549/65; 549/74; 549/75
[58] Field of Search ........ 260/329 R, 329 S, 329 AM, 260/326.82, 326.35, 326.5 SM, 326.84; 549/59, 74, 75, 65; 424/275, 274; 542/416

[56] References Cited

U.S. PATENT DOCUMENTS

| | | | |
|---|---|---|---|
| 2,519,325 | 8/1950 | Sondern et al. | 260/329 AM |
| 2,556,636 | 6/1951 | Sperber et al. | 260/329 AM |
| 2,604,473 | 7/1952 | Sperber et al. | 260/329 AM |

FOREIGN PATENT DOCUMENTS 1307539 2/1973 United Kingdom .
1338169 11/1973 United Kingdom .
1397436 6/1975 United Kingdom .
1421792 1/1976 United Kingdom .

*Primary Examiner*—Natalie Trousof
*Assistant Examiner*—L. Hendriksen
*Attorney, Agent, or Firm*—Bacon & Thomas

[57] ABSTRACT

Compounds of the general formula

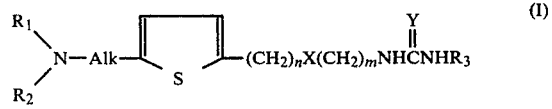

and physiologically acceptable salts, hydrates and bioprecursors thereof are disclosed, in which $R_1$ and $R_2$, which may be the same or different, represent hydrogen, lower alkyl, cycloalkyl, aralkyl or lower alkenyl groups, which alkyl groups may be interrupted by an oxygen atom or a group

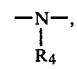

in which $R_4$ represents hydrogen or lower alkyl; or $R_1$ and $R_2$ may, together with the nitrogen atom to which they are attached form a heterocyclic ring which may contain other hetero functions selected from —O— and

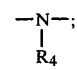

$R_3$ represents hydrogen, lower alkyl, lower alkenyl or alkoxyalkyl;
X represents —O—, —S— or —CH$_2$—;
Y represents =S, =O, =NR$_5$ or =CHR$_6$;
  in which R$_5$ is hydrogen, nitro, cyano, lower alkyl, aryl, alkylsulphonyl or arylsulphonyl and R$_6$ represents nitro, alkylsulphonyl or arylsulphonyl;
m is an integer from 2 to 4 inclusive;
n is 1 or 2 or, when X is S or CH$_2$, n is zero, 1 or 2 and Alk denotes a straight or branched alkylene chain of 1 to 6 carbon atoms.

The compounds have therapeutic activity. Further disclosed are the corresponding primary amines of the formula

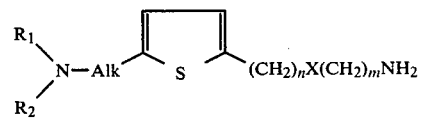

from which the above compounds may be prepared by introducing the group

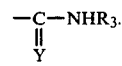

19 Claims, No Drawings

PHARMACOLOGICALLY ACTIVE COMPOUNDS

This invention relates to new aminoalkyl thiophene derivatives having a selective action on histamine receptors, to processes for the preparation thereof, and pharmaceutical compositions containing them, as well as their use in pharmacy.

A subdivision of histamine receptors (H-receptors) into two groups designated $H_1$- and $H_2$-receptors has been proposed by Ash and Schild (Brit. J. Pharmacol. Chemother, 1966, 27, 427) and Black et al (Nature 1972, 236, 385). Stimulation of bronchial and gastrointestinal smooth muscle is mediated through $H_1$-receptors and these effects can be prevented by conventional histamine antagonists such as mepyramine. Stimulation of gastric acid secretion and heart rate is mediated through $H_2$-receptors; these effects are not modified by mepyramine but are prevented or abolished by $H_2$-antagonists such as metiamide. Histamine stimulates $H_1$- and $H_2$-receptors.

We have found that certain novel aminoalkyl thiophene derivatives are selective $H_2$-antagonists, that is they show inhibition of the secretion of gastric acid when this is stimulated via histamine $H_2$-receptors (Ash and Schild loc. cit.). Their ability to prevent the secretion of gastric juice when it is stimulated via histamine $H_2$-receptors can be demonstrated in the perfused rat stomach, preparation described by Ghosh and Schild (Brit. J. Pharmacol. Chemother. 1958 13 54), modified as hereinafter described and in conscious dogs equipped with Heidenhain pouches using the same method as Black et al (Nature 1972 236 385). The compounds according to the invention do not modify histamine induced contractions of isolated gastrointestinal smooth muscle.

Compounds with histamine $H_2$-blocking activity may be used in the treatment of conditions where there is a hypersecretion of gastric acid e.g. in gastric and peptic ulceration, and in the treatment of allergic conditions where histamine is a known mediator. They may be used, either alone, or in combination with other active ingredients in the treatment of allergic and inflammatory conditions such as urticaria.

The present invention provides compounds of the general formula (I):

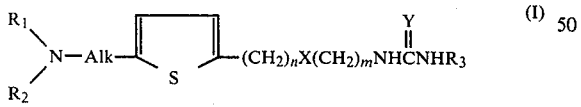

and physiologically acceptable salts, hydrates and bio-precursors thereof in which $R_1$ and $R_2$, which may be the same or different, represent hydrogen, lower alkyl, cycloalkyl, aralkyl or lower alkenyl groups which alkyl groups may be interrupted by an oxygen atom or a group

in which $R_4$ represents hydrogen or lower alkyl, or $R_1$ and $R_2$ may, together with the nitrogen atom to which they are attached, form a heterocyclic ring which may contain other hetero functions selected from —O— and

$R_3$ represents hydrogen, lower alkyl, lower alkenyl or alkoxyalkyl;

X represents —O—, —S— or —CH$_2$—;

Y represents =S, =O, =NR$_5$ or =CHR$_6$ in which

R$_5$ is hydrogen, nitro, cyano, lower alkyl, aryl, alkylsulphonyl or arylsulphonyl;

R$_6$ represents nitro, alkylsulphonyl or arylsulphonyl;

m is an integer from 2 to 4 inclusive;

n is 1 or 2; or when X is —S—, or —CH$_2$—, n is zero, 1 or 2 Alk denotes a straight or branched alkylene chain of 1 to 6 carbon atoms;

The term "lower as applied to "alkyl" means that the group has a small number of carbon atoms, preferably 1 to 6 carbon atoms, and in particular 1 to 4 carbon atoms and when applied to alkenyl, that the group has preferably 3 to 6 carbon atoms. The term "aryl" preferably means phenyl or substituted phenyl, for example phenyl substituted with alkyl, alkoxy or halogen.

All the compounds can exhibit tautomerism and the formula is intended to cover all tautomers. Where Alk denotes a branched chain alkylene group, optical isomers may exist, and the formula is intended to cover all diastereoisomers and optical enantiomers.

A preferred group of compounds according to the invention is that in which the following groups have the meanings given $R_1$ and $R_2$ represent independently hydrogen or lower alkyl or together with the adjacent nitrogen atom form a pyrrolidino ring;

Alk represents —CH$_2$—;

n is 1;

X has the meaning given above;

m is 2;

Y represents =NNO$_2$, =NCN, =S, =NSO$_2$CH$_3$ or =CHNO$_2$; and $R_3$ represents hydrogen, lower alkyl or alkoxyalkyl.

Particularly preferred compounds are those where $R_1$ and $R_2$ are hydrogen or methyl, X is sulphur, m is 2, n is 1, Alk is —CH$_2$—, Y is =CHNO$_2$. and $R_3$ is methyl.

Two preferred compounds are:

N-Methyl-N'-[2-[[[5-(N,N-dimethylaminomethyl)2-thienyl]methyl]thio]ethyl]2-nitro-1,1-ethenediamine N-Methyl-N'-[2-[[[5-(N-methylaminomethyl)2-thienyl]methyl]thio]ethyl]2-nitro-1,1-ethenediamine.

The compounds according to the invention readily form physiologically acceptable salts. Such salts include salts with inorganic acids such as hydrochlorides, hydrobromides and sulphates and salts with organic acids, particularly those formed with aliphatic mono- or di-carboxylic acids. Examples of carboxylic acid salts are acetates, maleates and fumarates. The compounds may also form hydrates.

The compounds according to the invention can be administered orally, topically or parenterally or by suppository, of which the preferred route is the oral route. They may be used in the form of the base or as a physiologically acceptable salt. They will in general be associated with a pharmaceutically acceptable carrier or diluent, to provide a pharmaceutical composition.

The compounds according to the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form. Suitable topical preparations include ointments, lotions, creams, powders and sprays.

A convenient daily dose by the oral route would be of the order of 100 mg to 2 g per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

For topical application a spray, ointment, cream or lotion may be used. These compositions may contain an effective amount of the active ingredient, for example of the order of 1½ to 2% by weight of the total composition.

The compounds of the present invention may be made from a primary amine of the formula:

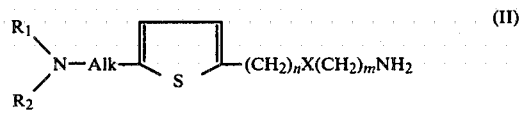

in which $R_1$, $R_2$, Alk, n, X and m have the meanings given herein with a compound capable of introducing the group

in which $R_3$ and Y have the meanings given herein. Compounds which are capable of introducing the group

are, isocyanates $R_3NCO$, isothiocyanates $R_3NCS$, or compounds of the formulae

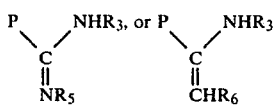

where P is a leaving group such as halogen, thiomethyl, 3,5-dimethylpyrazolyl or alkoxy, but is preferably thiomethyl. The reaction with the isocyanate or isothiocyanate may be carried out by allowing the amine and isocyanate or isothiocyanate to stand in a solvent such as acetonitrile. The reaction with the compound

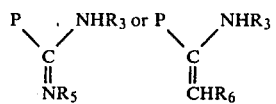

can be carried out by fusing the reactants at an elevated temperature e.g. 100°–120° C. Alternatively the amine (II) and the compound

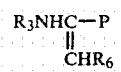

may be stirred in aqueous solution at room temperature. Where $R_3$ represents hydrogen, alkali metal cyanates and thiocyanates are used the reaction being effected at elevated temperature. Alternatively, organic isocyanates and isothiocyanates may be used e.g. ethylcarbonisothiocyanatidate, followed by basic hydrolysis.

In an alternative process the amine (II) is reacted with a compound of formula

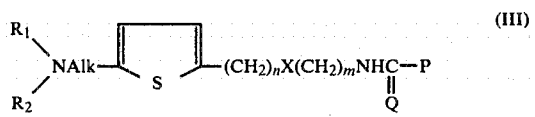

followed by reaction of the resulting compound of formula (III)

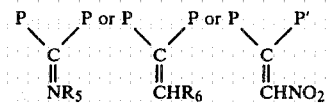

with an amine $R_3NH_2$. P' is a group SOA where A represents a lower alkyl group e.g. methyl. The group Q may be $NR_5$ or $CHR_6$. The first step of the reaction may be effected in a solvent, e.g. ethanol or acetonitrile at a temperature from ambient to reflux. The second stage of the reaction may be effected in a suitable solvent e.g. ethanol at a temperature from ambient to reflux.

Compounds of formula (I) in which n is 1, x is sulphur (and, when $R_1$ and $R_2$ are both hydrogen, Y is other than $CHR_6$) may also be prepared from a compound of formula (IV) or (V) using a thiol of formula (VI)

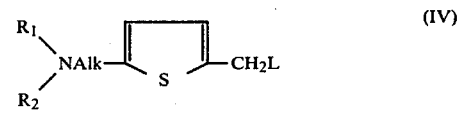

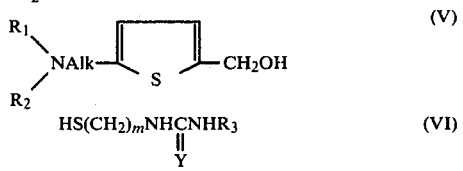

In the above formula (IV) L represents a leaving group e.g. halogen or acyloxy e.g. acetoxy. Where one is producing compounds in which $R_1$ and $R_2$ are hydrogen the amino group $NR_1R_2$ is protected in compounds of formulae (IV) and (V) as, for example, in the case of a primary amine, a phthalimido group in which case the protecting group may be removed at an appropriate stage in the reaction using a primary amine or a hydrazine e.g. methylamine or hydrazine hydrate.

The reaction between a thiol (VI) and a compound of formula (IV) is preferably carried out in the presence of a strong base e.g. sodium hydride at room temperature in an organic solvent e.g. dimethylformamide. The reaction between a thiol (VI) and a compound of formula (V) is preferably carried out at 0° C. in mineral acid e.g. concentrated hydrochloric acid. The starting materials of formula (IV) may be prepared from alcohols of formula (V) by conventional means.

Another process for preparing compounds according to the invention in which Y is sulphur and $R_1$ and $R_2$ are not both hydrogen from amines (II) involves treatment of the amine with carbon disulphide followed by reaction with a chloroformate ester e.g. ethyl chloroformate to give an isothiocyanate of formula (VII)

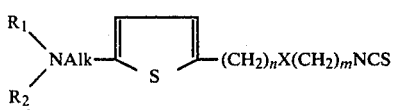

(VII)

where $R_1$, $R_2$, Alk, n, m and X have the meanings given above with the proviso that $R_1$ and $R_2$ are not both hydrogen.

When a compound of formula (VII) is reacted with an amine $R_3NH_2$, preferably in a solvent such as acetonitrile, the product is a compound of formula (I) where Y is sulphur and $R_1$ and $R_2$ are not both hydrogen.

Compounds of formula (I) where $R_1$ and $R_2$ are both methyl groups, Alk is methylene and Y is other than $=CHR_6$ may be prepared by treating a substituted thiophene of formula (VIII)

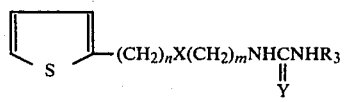

(VIII)

in which Y is other than $CHR_6$ with the reagent of the formula (IX)

(IX)

in a solvent e.g. acetonitrile at reflux temperature.

In the above discussion of the processes available for the production of compounds according to the invention, reference has been made to primary amines of formula (II). These amines are novel compounds and the invention includes such compounds and acid addition salts thereof. These intermediates may be made by a number of processes which are described below.

Amines of formula (II) where n is 1 and X is oxygen or sulphur may be prepared by reaction of a compound of formula (IV) with a compound capable of introducing the group $-X(CH_2)_mNH_2$ in which m is as defined above, or a group convertible thereto. An example of such a compound is a compound of formula (X)

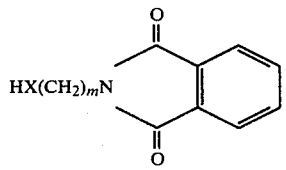

(X)

The protecting group may subsequently be removed by methods described above.

Amines in which n is 1 and X is sulphur may be prepared from alcohols of formula (V) by reaction with an aminothiol $HS(CH_2)_mNH_2$ in which m is as defined above. Alternatively such amines may be prepared from a thiol of formula (XI)

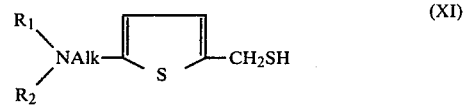

(XI)

by reaction with an ω-substituted alkylphthalimide (XII)

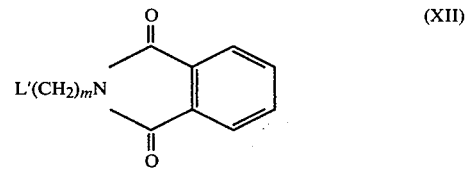

(XII)

where L' is as defined above for L or in addition may be a sulphonyloxy group e.g. mesyloxy or tosyloxy and m is as defined above. The protecting phthalimido group may subsequently be cleaved by conventional means as described above.

Amines of formula (II) where n is 1, X is sulphur and m is 2 can be obtained by treating a thiol of formula (XI) with ethylene imine.

The thiol of formula (XI) is obtained by standard procedures from a compound of formula (IV) or (V).

Amines of formula (II) where X is oxygen and n is 1 can be prepared from alcohols of formula (V) by reaction with a haloester Hal $(CH_2)_{m-1}CO_2E$ where E is alkyl e.g. methyl and Hal is halogen e.g. bromine. The resulting compound of formula (XIII)

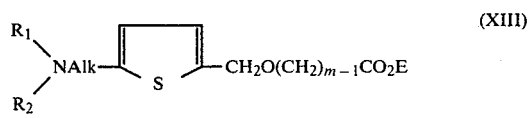

(XIII)

is then reacted with ammonia and the resulting amide is reduced with, for example, lithium aluminium hydride to give the amine (II) in which X is oxygen and n is 1.

Amines of formula (II) where X is sulphur, n is zero and $R_1$ and $R_2$ are other than hydrogen may be prepared from compounds of formula (XIV)

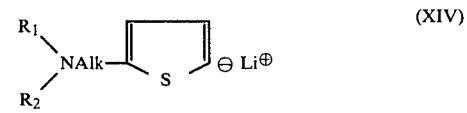

(XIV)

by treatment with elemental sulphur. The intermediate (XV) so formed

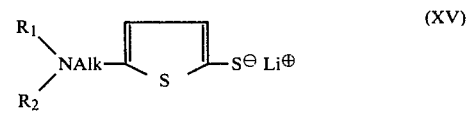

(XV)

may then be reacted with an ω-substituted alkylphthalimide (XII). The resulting protected amine of formula (XVI)

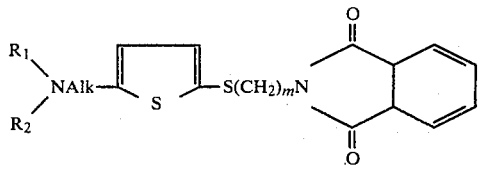
(XVI)

can then be deprotected as described above.

Amines (II) where X is CH$_2$, n is zero and R$_1$ and R$_2$ are other than hydrogen may be prepared from compounds (XIV) by reaction with a dihaloalkane e.g. Br(CH$_2$)$_{m+1}$Br followed by (a) treatment with ammonia or (b) treatment with potassium phthalimide followed by cleavage of the phthalimide group.

Amines of formula (II) where R$_1$ and R$_2$ are both methyl groups and Alk is methylene may be prepared from intermediates of formula (XVII)

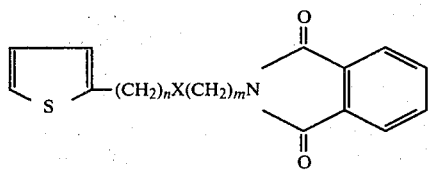
(XVII)

by treatment with the reagent of formula (IX) and subsequent removal of the protecting group.

Alternatively the reagent (IX) may be reacted with a compound of formula (XVIII)

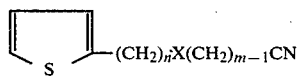
(XVIII)

followed by reduction of the nitrile group using, for example, lithium aluminium hydride.

Amines of formula (II) where Alk is methylene, n is 1 and X is oxygen or sulphur may be prepared by reduction of compounds of formula (XIX) using a suitable reducing agent e.g. lithium aluminium hydride.

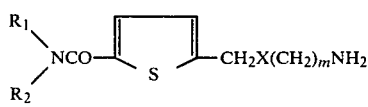
(XIX)

Compounds of formula (XIX) may be prepared from alcohols of formula (XX)

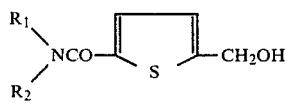
(XX)

by the means described above for converting the OH function of 2-thiophene methanols into a group —X(CH$_2$)$_m$NH$_2$.

Amines of formula (II) where X is sulphur, R$_1$ and R$_2$ are methyl, Alk is methylene and n is 2 may be prepared using a compound of formula (XXI)

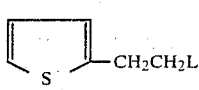
(XXI)

and reacting it with an ω-phthalimido alkylthiol. The resulting compound of formula (XXII)

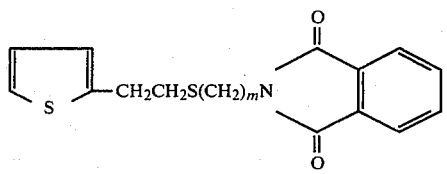
(XXII)

may be treated with the reagent (IX) to introduce the group (CH$_3$)$_2$NCH$_2$—. Subsequent cleavage of the phthalimido group then gives amines of formula (II) wherein X is S, R$_1$ and R$_2$ are methyl groups, Alk represents methylene and n is 2.

The substituent R$_1$R$_2$NAlk in the 5-position of the thiophene ring in the compounds of the invention may be introduced at any suitable stage of the reaction. The following are illustrations of how such groups may be introduced.

Thiophene-2-carboxylic acid may be converted into the corresponding acid halide e.g. chloride and the resulting acid halide treated with the appropriate amine R$_1$R$_2$NH to give an amide of formula (XXIII)

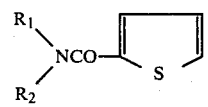
(XXIII)

The amide of formula (XXIII) may be converted into a compound of formula (XX) by hydroxymethylation using formaldehyde or a precursor of formaldehyde such as paraformaldehyde and a mineral acid.

The amide group in the resulting compound of formula (XX) may be reduced with a suitable reducing agent e.g. lithium aluminium hydride, to yield a compound of formula (V) in which Alk represents methylene.

The amide group in a compound of formula (XXIII) may be reduced in a similar manner to yield a compound of formula (XXIV)

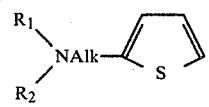
(XXIV)

in which Alk represents methylene.

Hydroxymethylation of a compound (XXIV) in which R$_1$ and R$_2$ are other than hydrogen to afford a compound of formula (V) in which R$_1$ and R$_2$ are other than hydrogen may be achieved by treating the derived thienyl anion (generated for example by means of n-butyl lithium) with formaldehyde.

The alcohol of formula (V) where R$_1$ and R$_2$ are both methyl groups and Alk represents methylene may be prepared from 2-thiophene methanol (XXV)

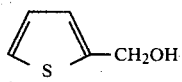
(XXV)

by treatment with the reagent of formula (IX).

Similarly, 2-thienylacetic acid is a useful starting material from which to obtain both 2-(2-thienyl)ethanol and compounds of formula (XXVI)

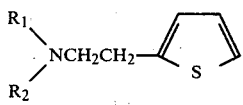
(XXVI)

which can then be used in analogous fashions to prepare amines of formula (II) where Alk is —$CH_2CH_2$— or n is 2.

When the alkylene chain Alk is greater than two carbon atoms, a lithio derivative, prepared by reacting thiophene with butyl lithium may be used as starting material. This may be treated sequentially with (i) a dihaloalkane of formula Hal Alk Hal where Hal represents e.g. bromine and (ii) an amine $R_1R_2NH$ to give a compound of formula (XXIV) where Alk contains from 3 to 6 carbon atoms. Where side chains in which both $R_1$ and $R_2$ are hydrogen atoms are required, potassium phthalimide may replace the amine $R_1R_2NH$. In this case, hydroxymethylation is conveniently carried out on the protected compound, followed by deprotection to give an alcohol of formula (V) in which both $R_1$ and $R_2$ are hydrogen.

If compounds where $R_1$ and $R_2$ are other than hydrogen are required, the primary and secondary amino compounds can be converted into N-substituted compounds at a suitable stage, for example by the use of an alkyl or aralkyl halide or formaldehyde and formic acid in the Eschweiler-Clarke procedure. It is however preferable to use the substituted amine at the appropriate stage in the reaction.

In order that the invention may be more fully understood the following Examples are given by way of illustration only. Preceding the Examples are a number of Preparations describing the production of intermediates. (In the Preparations and Examples, the TLC measurements were carried out on silica gel plates of thickness 0.25 mm mounted on a plastic support, the N.m.r. data is recorded in $\tau$ values and pressure is expressed in mm. of mercury.)

PREPARATION I

N-[(2-Thienyl)methyl]pyrrolidine

N-(2-Thienylcarbonyl)pyrrolidine

Pyrrolidine (47 ml) was added to 2-thiophene carbonyl chloride (40 g) in toluene below 10°. After 1½ hr, water was added. The product was extracted with ethyl acetate, crystallised from toluene and recrystallised from light petroleum (b.p. 60°-80°)/ethyl acetate to give white crystals (40 g) m.p. 66°-68°; TLC silica-/ethyl acetate Rf 0.5.

N-[(2-Thienyl)methyl]pyrrolidine

Lithium aluminium hydride (9.6 g) was added to N-(2-thienylcarbonyl)pyrrolidine (35.4 g) in ether. After 4½ hr the reaction was quenched with water and extracted with chloroform. Evaporation of the organic extracts gave an oil which was distilled under reduced pressure (21.5 g) b.p. 60°-70° (10-16 mm). TLC silica-/ethyl acetate, methanol, Rf 0.7.

PREPARATION II

N-Ethyl-N-methyl-2-thiophene methanamine

Bromoethane (150 ml), triethylamine (7.3 ml) and N-methyl-2-thiophenemethanamine (21.2 g) were stirred at room temperature in toluene (212 ml) for 4 days. The solution was diluted with water, saturated with sodium bicarbonate and extracted with ethyl acetate. The organic extracts were distilled to give the title compound as an oil (13.6 g) b.p. 46° (16 mm).

PREPARATION III 5-(N,N-Dimethylaminomethyl)2-thiophenemethanol

Route (i)

A mixture of 2-thiophenemethanol (1.14 g) and N,N-dimethylimminium chloride (1.4 g) was heated at reflux in dry acetonitrile (10 ml) for 5 hr. The reaction was cooled, basified with sodium hydroxide, and extracted with ethyl acetate. The organic phase was distilled to give the title compound as an oil (0.97 g) b.p. 140° (0.01 mm). TLC silica/ethanol:ethyl acetate (1:1) Rf 0.4.

Route (ii)

Formaldehyde gas, generated by the thermal depolymerisation of paraformaldehyde (0.9 g) was passed, by a stream of nitrogen, into a solution of dimethylamine hydrochloride (1.2 g) and 2-thiophenemethanol (1.14 g) in dry acetonitrile at reflux. After 5 hr, the reaction was cooled, basified with sodium hydroxide, and extracted with ethyl acetate. The organic extract was distilled to afford the title compound as an oil (0.34 g) b.p. 140° (0.01 mm). TLC Silica/ethanol:ethyl acetate (1:1) Rf 0.4.

Route (iii)

(a) 5-(N,N-dimethylaminomethyl)2-thiophenemethanol n-Butyl lithium (1.6 M in hexane; 62 ml) was added at room temperature to a solution of N,N-dimethyl-2-thiophenemethanamine (13.7 g) in dry tetrahydrofuran under a nitrogen atmosphere. The reaction was stirred for 4 hr at room temperature, cooled to 5° and treated with formaldehyde gas, generated by the thermal depolymerisation of paraformaldehyde (6.0 g). The reaction mixture was stirred for a further 30 minutes, treated with water and extracted with dichloromethane. The organic phase was dried and evaporated to give an oil (10.1 g) b.p. 140° (1×10$^{-2}$ mm). TLC (silica, ethanol/ethyl acetate 1:1) Rf 0.4.

Similarly prepared from the corresponding thiophene (A) and n-butyl lithium were:

(b) 5-(N-Ethyl-N-methylaminomethyl)2-thiophenemethanol (4.1 g) b.p. 134° (3 mm). TLC silica/ethyl acetate, water, isopropanol, 0.88 ammonia, 25:8:15:2; Rf 0.70 from (A) (12.6 g) and n-butyl lithium (48 ml).

(c) 5-[(N-Pyrrolidino)methyl]2-thiophenemethanol (14.65 g) b.p. 146° (0.5 mm). TLC silica/ethyl acetate, water, isopropanol, 0.88 ammonia 25:8:15:2, Rf 0.85 from (A) (16.5 g) and n-butyl lithium (65 ml).

PREPARATION IV

5-(N,N-Dimethylaminomethyl)-2-thienyl-4-butanamine dioxalate 2-(4-Bromobutyl)-thiophene n-Butyl lithium in hexane (171.9 ml) was added to thiophene (21 g) in dry tetrahydrofuran (240 ml) and the mixture was stirred at room temperature for 2 hr. 1,4-Dibromobutane (59.4 g) in tetrahydrofuran (50 ml) was added over 178 hr at 0° and the reaction was stirred at room temerature for 17 hr. Water was added and the product was extracted with ethyl acetate. Distillation of the extracts gave a pale oil (26.83 g) b.p. 95°–100° (0.2 mm). TLC silica/15% methanol; ethyl acetate; Rf 0.90.

N-[4-(4-Thienyl)butyl]1H-isoindole-1,3(2H)-dione

A suspension of 4-bromobutyl-2-thiophene (15.4 g) and potassium phthalimide (15.6 g) in dimethylformamide (150 ml) was stirred at room temerature for 64 hr. Water was added to precipitate the title compound as a white solid (17.8 g) m.p. 92°–93.5°. TLC Silica/light petroleum b.p. 60°–80°; ethyl acetate (3:1) Rf 0.40.

N-[4-D[5-(N,N-dimethylaminomethyl)2-thienyl]-butyl]1H-isoindole-1,3(2H)-dione hydrochloride A solution of N-[4-(2-thienyl)butyl]1H-isoindole-1,3(2H)-dione (1.43 g) and N,N-dimethyliminium chloride (0.95 g) in acetonitrile (20 ml) was heated at reflux for 17 hr. The reaction solution was cooled to give the title compound as a white crystalline solid (1.8 g) m.p. 129.5°–131°. TLC Silica/ethyl acetate, water, isopropanol, 0.88 ammonia (25:8:15:2) Rf 0.95.

5-(N,N-Dimethylaminomethyl)-2-thienyl-4-butanamine dioxalate

N-[4-[5-(N,N-Dimethylaminomethyl)2-thienyl]-butyl]1H-isoindole-1,3(2H)-dione hydrochloride (15.3 g) was treated with sodium hydroxide and extracted with ethyl acetate. Evaporation of the organic extracts gave an oil which was heated at reflux with hydrazine hydrate (2.5 g) in ethanol (100 ml) for 5 hr. Solvent was removed, the residue was basified and extracted with ethyl acetate. Addition of ethanolic oxalic acid gave the title compound as white crystals (9.58 g) m.p. 157.5°–159°. TLC silica/ethyl acetate, water, isopropanol, 0.88 ammonia, 25:8:15:2, Rf 0.20.

PREPARATION V

(a)

2-[[[5-(N,N-Dimethylaminomethyl)2-thienyl]methyl]thio] ethanamine 5-(N,N-dimethylaminomethyl)thiophenemethanol (6.92 g) was added at 2°–4° to a solution of cysteamine hydrochloride (4.6 g) in concentrated hydrochloric acid (15 ml). The reaction mixture was stirred at room temerature for 3½ hr then diluted with ethyl acetate (100 ml) and basified with solid sodium carbonate. Magnesium sulphate was added, the solids were filtered off and the filtrate was evaporated to an oil (2.8 g) b.p. 180° ($2 \times 10^{-2}$ mm). TLC silica; EtOAc/i-PrOH/H$_2$O/0.88 NH$_3$ (25:15:8:2) Rf 0.6.

Similarly prepared from the corresponding thiophenemethanol (B) and cysteamine hydrochloride were:

(b) N-2-[[[5-[(1-Pyrrolidino)methyl]2-thienyl]methyl]thio] ethanamine bis oxalate salt (14.11 g) m.p. 168°–170° TLC silica/ethyl acetate:isopropanol:water:0.880 ammonia 25:15:8:2, Rf 0.5 from (B) (7.9 g) and cysteamine hydrochloride (6.8 g).

(c) N-2-[[[5-(N-Methyl-N-ethylaminomethyl)2-thienyl]methyl] thio]ethanamine, bis oxalate salt (2.9 g) m.p. 157°–158°. TLC silica/ethyl acetate:isopropanol:water:0.880 ammonia; 25:15:8:2; Rf 0.65. from (B) (1.86 g) and cysteamine hydrochloride (1.7 g).

EXAMPLE 1

N-[2-[[[5-(N,N-Dimethylaminomethyl)-2-thienyl]methyl]thio] ethyl]N'-methylthiourea Methylisothiocyanate (0.22 g) in dry acetonitrile (2.5 ml) was added to a solution of 2-[[[5-(N,N-dimethylaminomethyl)2-thienyl]methyl]thio]ethanamine (0.69 g) in dry acetonitrile (0.25 ml). After 2 hr, the reaction mixture was evaporated and the residue was purified by column chromatography (silica; ethyl acetate/methanol 1:1) to give the product as a pale yellow viscous oil (0.57 g). TLC (silica; EtOAc/MeOH 1:1) Rf 0.5. Analysis Found: C, 47.15; H, 6.95; N, 13.8; S, 31.6. $C_{12}H_{21}N_3S_3$ requires: C 47.5; H, 6.95; N, 13,85; S, 31.65%.

EXAMPLE 2

N''-Cyano-N-[2-[[[5-(N,N-dimethylaminomethyl)2-thienyl]methyl]thio]ethyl]N'-methylguanidine An intimate mixture of 2-[[[5-(N,N-dmethylaminomethyl)2-thienyl]methyl]thio]ethanamine (0.69 g) and N-cyano-methylcarbamimidothioic acid methyl ester (0.39 g) was heated up to 120° over 1 hr and was maintained at this temperature for a further 1½ hr. During the heating period the reaction was intermittently evacuated to remove methanethiol. The resultant red gum was chromatographed (silica/ethyl acetate/methanol 1:1) to give a pale yellow oil (0.35 g). TLC silica; EtOAc/i-PrOH/-H$_2$O/0.880 NH$_3$ (25:25:8:2) Rf 0.5. NMR (CDCl$_3$) 3.1–3.3, q, (2H); 4.0, br q, (1H); 4.4 br t (1H); 6.08, s, (2H); 6.39, s, (2H); 6.59, q, (2H); 7.14, d, (3H); 7.28, m, (2H); 7.72, s, (6H).

EXAMPLE 3

N-Methyl-N'-[2-[[[5-(N,N-dimethylaminomethyl)2-thienyl]methyl]thio]ethyl]2-nitro-1,1-ethenediamine A solution of 2-[[[5-(N,N-dimethylaminomethyl)2-thienyl]methyl]thio]ethanamine (1.15 g) and 1-nitro-2,2-bis(methyl-thio)ethylene (0.83 g) in acetonitrile (100 ml) was heated under reflux for 1 hr. Evaporation of the solution in vacuo gave a viscous orange oil (2.1 g) which was used without further purification.

The oil was treated with ethanolic methylamine (33%, 13 ml) and heated under reflux for 16 hr. The solvent was then removed and the residue purified by column chromatography on silica using ethyl acetate/-methanol (1:1). The resultant pale yellow oil was triturated with ether to give a white crystalline solid (0.79 g) m.p. 60°–65°. TLC silica/ethanol: ethyl acetate (1:1) Rf 0.5.

EXAMPLE 4

N-Methyl-N'-[2-[[5-(N,N-dimethylaminomethyl)2-thienyl]methoxy]ethyl]2-nitro-1,1-ethenediamine

[[5-(N,N-Dimethylaminomethyl)-2-thienyl]methoxy]acetic acid ethyl ester

A 50% dispersion of sodium hydride in oil (4.8 g) was added to a solution of 5-(N,N-dimethylaminomethyl)-2- thiophene-methanol (17.1 g) in dry dimethylformamide (135 ml) at 3°. Ethyl bromo acetate (16.7 g) was added and the reaction was stirred at room temperature for 3 hr. Water was added and the mixture extracted with chloroform. The organic phase was dried and evaporated to an oil which was purified by column chromatography on silica gel, using ethyl acetate as eluent, followed by distillation to give a colourless oil (4.7 g) b.p. 130°–150° (0.05 mm). TLC silica/methanol: ethyl acetate (1:1) Rf 0.5.

[[5-(N,N-Dimethylaminomethyl)2-thienyl]methoxy]acetamide

A solution of [[5-(N,N-dimethylaminomethyl)2-thienyl]methoxy] acetic acid ethyl ester (4.0 g) in a mixture of 0.88 ammonia solution (75 ml) and ethanol (75 ml) was stirred for 1 hr at room temperature. The solvent was removed and the residue recrystallised from a 1:1 mixture of benzene and petroleum spirit (b.p. 60°–80°) to afford a white crystalline solid (3.2 g) m.p. 86.5°–95°. NMR (CDCl$_3$) 7.71, s, (6H); 6.38, s, (2H); 6.00, s, (2H); 5.30, s, (2H); 3.5, br, (2H); 3.12, q, (2H).

2-[[5-(N,N-dimethylaminomethyl)2-thienyl]methoxy]ethanamine

A suspension of lithium aluminium hydride (0.38 g) and [[5-(N,N-dimethylaminomethyl)2-thienyl]methoxy]acetamide (2.28 g) in a mixture of dry ether (25 ml) and dry tetrahydrofuran (5 ml) was heated at reflux for 4 hr. The reaction was then quenched with water and evaporated. The residue was extracted with chloroform. The organic phase was dried and distilled to afford a colourless oil (1.6 g) b.p. 110°–120° (0.1 mm). NMR (CDCl$_3$), 8.43, s, (2H); 7.72, s, (6H); 7.12, t, (2H); 6.46 t, (2H); 6.38, s, (2H); 5.32, s, (2H), 3–3.3, m, (2H).

N-Methyl-N'-[2-[[5-(N,N-dimethylaminomethyl)2-thienyl]methoxy]ethyl]2-nitro-1,1-ethenediamine
2-[[5-(N,N-Dimethylaminomethyl)2-thienyl]methoxy]ethanamine (0.6 g) and
1-nitro-2,2-bis(methylthio)ethylene (0.46 g) were refluxed in dry acetonitrile for 7 hr. Evaporation of the reaction solution gave an oil which was used without further purification. The oil was dissolved in a 33% solution of methylamine in ethanol (25 ml) and heated under reflux for 2 hr. The solvent was removed and the residual oil was purified by preparative thin layer chromatography on silica using methanol to give a pale yellow solid. Recrystallisation from ether afforded a white solid (0.43 g) m.p. 77.5°–80°. TLC silica/methanol, Rf 0.26.

EXAMPLE 5

N-Methyl-N'-[2-[[[5-(N-methylaminomethyl)2-thienyl]methyl]thio]ethyl]2-nitro-1,1-ethenediamine N-Methyl-(5-hydroxymethyl)2-thiophene carboxamide N-Methyl-2-thiophene carboxamide (28.5 g), paraformaldehyde (9.0 g) and conc. hydrochloric acid (60 ml) were stirred at room temperature for 10 days. The mixture was poured onto water, basified with sodium bicarbonate, and extracted with ethyl acetate. The organic extracts were column chromatographed (silica/ethyl acetate) to give a white crystalline solid (9.3 g) m.p. 119°–123°. TLC silica/ethyl acetate:isopropanol:water:0.88 ammonia 25:15:8:2, Rf 0.65.

N-Methyl-5-[[[2-aminoethyl]thio]methyl]thiophene-2-carboxamide

N-Methyl-(5-hydroxymethyl)2-thiophenecarboxamide (3.75 g), cysteamine hydrochloride (5.1 g) and conc. hydrochloric acid (30 ml) were heated at 60° for 4 hr. The reaction was cooled, basified with sodium hydroxide, and extracted with ethyl acetate. The organic extracts were chromatographed [silica/ethyl acetate:methanol (2:1)] to give the required compound as a pale yellow oil (4.1 g). TLC silica/ethyl acetate:isopropanol:ammonia:water (25:15:2.8) Rf 0.55. NMR (CDCl$_3$) 8.38, s, (2H); 7.25, m, (4H), 7.04, d, (3H); 6.10, s, (2H); 3.50, br, (1H), 3.07, d, (1H); 2.60, d, (1H).

2-[[[5-(N-Methylaminomethyl)2-thienyl]methyl]thio]ethanamine

N-Methyl-5-[[[(2-aminoethyl)]thio]methyl]thiophene-2-carboxamide (3.0 g) in tetrahydrofuran was treated with lithium aluminium hydride (2.0 g). The suspension was heated at 50° for 3 hr, cooled, treated with water, adjusted to pH 7 with dilute hydrochloric acid, and extracted with chloroform. The chloroform extracts were evaporated and the residue chromatographed (silica/ethyl acetate:methanol:ammonia: 20:80:2) to give a yellow oil (0.3 g). TLC (silica/ethyl acetate, water, isopropanol, 0.88 ammonia 25:8:15:2) Rf 0.5. NMR (CDCl$_3$) 8.52, s, (3H); 7.55, s, (3H); 7.0–7.5, m, (4H); 6.12, s, (4H); 3.23, t, (2H).

N-Methyl-N'-[2-[[[5-(N-methylaminomethyl)2-thienyl]methyl]thio]ethyl]2nitro-1,1-ethenediamine N-Methyl-2-nitroimidothioic acid methyl ester (0.25 g) and 2-[[[5-(N-methylaminomethyl)2-thienyl]methyl]thio]ethanamine (0.17 g) were stirred in water at room temperature for 18 hr. The solvent was removed and the residue chromatographed (silica/methanol) to give the title compound as a yellow oil (0.2 g). TLC silica/ethyl acetate:isopropanol:ammonia:water (25:15:2:8) Rf 0.6. NMR (CDCl$_3$) 7.50, s, (3H), 6.8–7.3, m, (5H); 6.8–7.3; m, (5H); 6.6 br, (2H); 6.08, s, (4H); 3.43, s, (1H); 3.20, s, (2H).

EXAMPLE 6

(a)

N-[4-[5-(N,N-Dimethylaminomethyl)2-thienyl]butyl]N'-methyl-2-nitro-1,1-ethenediamine Sodium hydroxide (1.76 g) and N-methyl-2-nitroimidothioic acid methyl ester (1.63 g) were added to a stirred solution of 5-(N,N-dimethylaminomethyl)2-thienyl-4-butanamine dioxalate (3.92 g) in water (60 ml) at room temperature. After 70 hr the water was evaporated to leave a yellow residue which was purified by column chromatography (silica/methanol) to give the title compound as a yellow solid (2.05 g). m.p. 104.5°–106° TLC silica/methanol, Rf 0.25.

Similarly prepared from the corresponding amine dioxalate (c) and N-methyl-2-nitroimidothioic acid methyl ester were:
(b)  N-Methyl-N'-[2-[[5-(1-pyrrolidino)methyl]2-thienylmethyl]thio]ethyl]-2-nitro-1,1-ethenediamine (1.87 g) TLC silica/methanol Rf 0.20. NMR (CDCl$_3$) 8–8.4, m, (4H); 6.8–7.6, m, (9H); 6.55, m, (2H); 6.18, s, (2H); 6.07; s, (2H); 3.4, s, (1H); 3.2, m, (2H); 2.8, br, (1H); -0.3, br, (1H) from (c) (8.7 g) and N-methyl-2-nitroimidothioic acid methyl ester (3.26 g).

(c) N-Methyl-N-[2-[[[5-(N-methyl-N-ethylaminomethyl)2-thienyl]methyl]thio]ethyl]2-nitro-1,1-ethenediamine (0.46 g) TLC silica/methanol Rf 0.4; NMR (CDCl$_3$) 8.9, t, (3H); 7.72; s, (3H); 7.46, q, (2H); 6.8–7.8, m, (5H); 6.6, m, (2H); 6.3, s, (2H); 6.08, s, (2H); 3.42, s, (1H); 3.2, m, (2H) from (c) (1.07 g) and N-methyl-2-nitroimidothioic acid methyl ester (0.44 g).

EXAMPLE 7

N-Nitro-N'-[[[[5-(N,N-dimethylaminomethyl)2-thienyl]methyl]thio]ethyl]guanidine

A suspension of N-nitrocarbamimidothioic acid methyl ester (1.05 g) and 2-[[[5-(N,N-dimethylaminomethyl)2-thienyl]methyl]thio]ethanamine (1.6 g) in ethanol (10 ml) was heated at 45° for 10 min. The resultant solid was recrystallised from ethyl acetate to give the title compound as white crystals (1.15 g) m.p. 118°–118.5°. TLC silica/methanol, Rf 0.40.

EXAMPLE 8

N-Methoxyethyl-N'-[2-[[[5-(N,N-dimethylaminomethyl)2-thienyl]methyl]thio]ethyl]2-nitro-1,1-ethenediamine 2-[[[5-(N,N-Dimethylaminomethyl)2-thienyl]methyl]thio]ethanamine (4.3 g) and 1-nitro-2,2-bis(methylthio)ethylene (3.3 g) in ethanol (50 ml) were heated at reflux for 5½ hr. Methoxyethylamine (1.8 ml) was added and the reaction heated at reflux for 22 hr. The solvent was removed and the residual oil was purified by column chromatography (silica/methanol). The resultant solid was recrystallised from isopropyl acetate to give the title compound as a white solid (1.04 g). m.p. 79°–80°. TLC silica/ethyl acetate, water, isopropanol, 0.88 ammonia 25:8:15:2, Rf 0.7.

EXAMPLE 9

N-[4-[5-(N,N-Dimethylaminomethyl)2-thienyl]butyl]N'-methanesulphonyl-N''-methylguanidine Methanesulphonyliminodithiocarbamic acid dimethyl ester (1.09 g) and 5-(N,N-dimethylaminomethyl)2-thienyl-4-butanamine (1.06 g) in ethanol (35 ml) were heated at reflux for 4½ hr. Ethanolic methylamine (15 ml) was added and the solution refluxed for 2 hr. The solvent was removed and the oil was purified by column chromatography (silica/methanol) to give the title compound as a viscous yellow oil (1.06 g). TLC silica/methanol, Rf 0.35. NMR (CDCl$_3$) 3.3, q, (2H); 3.9, br, m, (1H); 6.38, br, s, (2H); 6.7, m, (2H); 7.04, s, (3H); 6.9–7.4, m, (5H); 7.69, s, (6H); 8–8.5, m, (4H).

EXAMPLE 10

Pharmaceutical Compositions

| (a) Oral Tablets 50 mg | for 10,000 tablets |
| --- | --- |
| Active ingredient | 500 g |
| Anhydrous lactose U.S.P. | 2.17 kg |
| Sta-Rx 1500 Starch* | 300 g |
| Magnesium Stearate B.P. | 30 g |

The drug is sieved through a 250 μm sieve and then the four powders are intimately mixed in a blender and compressed between 8.5 mm diameter punches in a tabletting machine.

| (b) Injection for Intravenous administration (50 mg in 2 ml) | | |
| --- | --- | --- |
| | | % w/w |
| Active ingredient | | 2.5 |
| Water for Injections BP | to | 100.0 |
| Dilute hydrochloric acid BP | to | pH 5.0 |

The active ingredient is dissolved with mixing in the Water for Injection, adding the acid slowly until the pH is 5.0. The solution is sparged with nitrogen and is then clarified by filtration through a membrane filter of pore size 1.35 μm. It is packed into 2 ml glass ampoules (2.2 ml in each) and each ampoule sealed under an atmosphere of nitrogen. The ampoules are sterilised in an autoclave at 121° for thirty minutes.

| (c) Oral Sustained Release Tablets 150 mg | |
| --- | --- |
| | for 10,000 tablets |
| Active ingredient | 1.50 kg |
| Cutina HR** | 0.40 kg |
| Anhydrous lactose U.S.P. | 2.060 kg |
| Magnesium Stearate BP | 40 g |

The active ingredient, anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidised bed dryer. The granules are then passed through a 0.85 mm aperture sieve, blended with the magnesium stearate and compressed to a hardness of at least 10 kg (Schleuniger tester) on a tabletting machine with 12.5 mm diameter punches.

| Oral Capsules 50 mg | for 10,000 capsules |
| --- | --- |
| Active ingredient | 500 g |
| Sta-Rx 1500* | 1700 g |
| Magnesium Stearate BP | 20 mg |

The drug is sieved through a 250 μm mesh sieve and is then blended with the other powders. The powder is filled into No. 3 size hard gelatin capsules on a suitable filling machine.

The compounds of the formula (I) have been found to be inhibitors of gastric acid secretion induced by histamine. This has been shown in rats using a modification of the procedure described by M. N. Ghosh and H. O. Schild in the British Jounral of Pharmacology 1958, Vol. 13, page 54.

Female rats weighing about 150 g are starved overnight and provided with 8% sucrose in normal saline instead of drinking water.

The rats are anaesthetized by a single intraperitoneal injection of 25% w/v urethane solution (0.5 ml/100 g) and the trachea and jugular veins cannulated.

A mid-line incision in the abdomen wall is made to expose the stomach which is separated from the liver and spleen by cutting the connective tissue. A small opening is made in the fundic region of the stomach and the stomach washed with a 5% dextrose solution. The oesophagus is cannulated with rubber tubing and the oesophagus and vagi are then cut above the cannula.

A small opening is then made in the pyloric region of the stomach. A large perspex cannula is then placed in the stomach via the opening in the fundic region in such a manner that the inlet end of the cannula passes out of the stomach through the opening in the pyloric region. The cannula is of such a shape so as to reduce the effective volume of the stomach and to provide a turbulent flow of the perfusion fluid over the mucosal surface. A drainage cannula is then inserted through the opening in the fundic region of the stomach. Both cannulae are tied in place by ligatures around the stomach, positioned to avoid the main blood vessels. Stab wounds are made in the body wall and the cannulae passed through. The stomach is perfused through the oesophageal and pyloric cannulae with 5% dextrose solution at 39° C. at a rate of 1.5 ml/min. for each cannula. The effluent is passed over a micro-flow pH electrode and recorded via a pH meter and flat bed recorder.

The basal output of acid secretion from the stomach is monitored by measurement of the pH of the perfusion effluent and then increased acid secretion is induced by a continuous intravenous infusion of a sub-maximal dose of histamine; this produces a stable plateau of acid secretion and the pH of the perfusion effluent is determined when this condition is obtained.

The test compound is then administered to the rat by an intravenous injection and the change in 'gastric' acid secretion is monitored by measuring the change in the pH of the perfusion effluent.

From the change in pH of the perfusion effluent, the difference in acid secretion between basal output and the histamine stimulated plateau level is calculated as hydrogen ion concentration in mole/l. The reduction of acid secretion caused by the administration of the test compound is also calculated as the change in hydrogen ion concentration in mole/l from the difference in the pH of the perfusion effluent. The percentage reduction in acid secretion caused by the administration of the test compound may then be calculated from the two figures obtained.

$ED_{50}$ values for inhibition of acid secretion are determined by administering one dose of the test compound to one rat and repeating this in at least four rats for each of three or more dose levels. The results obtained are then used to calculate the $ED_{50}$ value by the standard method of least squares, as used for any dose response line.

We claim:

1. A compound of the formula

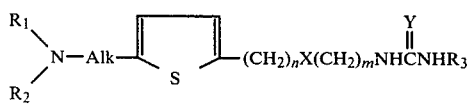
(I)

and physiologicially acceptable salts and hydrates thereof, in which
$R_1$ and $R_2$, which may be the same or different, represent hydrogen or lower alkyl, or
$R_1$ and $R_2$, together with the nitrogen atom to which they are attached form the pyrrolidino ring;
$R_3$ represents hydrogen, lower alkyl, lower alkenyl or alkoxyalkyl;
X represents —O—, —S— or —CH$_2$—;
Y represents =S, =O, =NR$_5$ or =CHR$_6$; in which R$_5$ is hydrogen, nitro, cyano, lower alkyl, aryl, alkylsulphonyl or arylsulphonyl and R$_6$ represents nitro, alkylsulphonyl or arylsulphonyl;

m is an integer from 2 to 4 inclusive;
n is 1 or 2 or, when X is S or CH$_2$, n is zero, 1 or 2; and Alk denotes a straight or branched alkylene chain of 1 to 6 carbon atoms.

2. A compound as claimed in claim 1 in which Alk represents a methylene group.

3. A compound as claimed in claim 1, in which n is 1 and m is 2.

4. A compound as claimed in claim 1, in which Y represents =S, =NNO$_2$, =NCN, =NSO$_2$CH$_3$ or =CHNO$_2$.

5. A compound as claimed in claim 1 in which X is a sulphur atom.

6. A compound as claimed in claim 1 in which
Alk represents —CH$_2$—;
n is 1;
X represents —O—, —S— or —CH$_2$—;
m is 2;
Y represents =NNO$_2$, =NCN, =S, =NSO$_2$CH$_3$ or =CHNO$_2$; and
R$_3$ represents hydrogen, lower alkyl or alkoxyalkyl.

7. A compound as claimed in claim 1 in which $R_1$ and $R_2$ are hydrogen or methyl, X is sulphur, m is 2, n is 1, Alk is —CH$_2$—, Y is =CHNO$_2$ and $R_3$ is methyl.

8. Compounds as defined in claim 1 wherein Y represents =CHR$_6$.

9. A compound as claimed in claim 1 which is N-Methyl-N'-[2-[[[5-(N,N-dimethylaminomethyl)2-thienyl]methyl]thio]ethyl]2-nitro-1,1-ethenediamine.

10. A compound as claimed in claim 1 which is N-Methyl-N'-[2-[[[5-(N-methylaminomethyl)2-thienyl]-methyl]thio]ethyl]2-nitro-1,1-ethenediamine.

11. A compound of formula II that is:

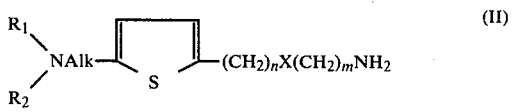
(II)

in which $R_1$, $R_2$, Alk, n, X and m have the meanings given in claim 1.

12. A pharmaceutical composition for treating a condition of hypersecretion of gastric acid mediated through histamine H$_2$-receptors comprising an effective amount of a compound as claimed in claim 1 in association with a pharmaceutically acceptable carrier or diluent.

13. A composition as claimed in claim 12 in a form suitable for oral, topical or parenteral administration or administration by suppository.

14. A composition as claimed in claim 13 in oral form as tablets.

15. A composition as claimed in claim 14 in the form of slow release tablets.

16. A composition as claimed in claim 14 or 15 containing 20 to 200 mg of active ingredient per tablet.

17. A composition as claimed in claim 13 in topical form as a spray, ointment or cream.

18. A method of treating a condition of hypersecretion of gastric acid mediated through histamine H$_2$-receptors which comprises administering to a patient an effective amount of a compound as claimed in claim 1 to relieve said condition.

19. A method as claimed in claim 18 in which the condition is peptic ulceration.

* * * * *